(12) United States Patent
Melman (10) Patent No.: US 12,138,046 B2
(45) Date of Patent: Nov. 12, 2024

(54) SYSTEM AND METHOD FOR TINNITUS SUPPRESSION

(71) Applicant: Cochlear Limited, Macquarie University (AU)

(72) Inventor: Ryan Orin Melman, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 230 days.

(21) Appl. No.: 17/425,282

(22) PCT Filed: Mar. 11, 2020

(86) PCT No.: PCT/IB2020/052172
§ 371 (c)(1),
(2) Date: Jul. 22, 2021

(87) PCT Pub. No.: WO2020/188415
PCT Pub. Date: Sep. 24, 2020

(65) Prior Publication Data
US 2022/0117518 A1    Apr. 21, 2022

Related U.S. Application Data

(60) Provisional application No. 62/819,774, filed on Mar. 18, 2019.

(51) Int. Cl.
*A61B 5/12* (2006.01)
*A61B 5/00* (2006.01)
(Continued)

(52) U.S. Cl.
CPC .............. *A61B 5/128* (2013.01); *A61B 5/372* (2021.01); *A61B 5/38* (2021.01); *A61B 5/4836* (2013.01);
(Continued)

(58) Field of Classification Search
None
See application file for complete search history.

(56) References Cited

U.S. PATENT DOCUMENTS 6,682,472 B1    1/2004  Davis
6,785,394 B1 *  8/2004  Olsen ................... H04R 25/505
                                               381/323
(Continued)

FOREIGN PATENT DOCUMENTS

CN        1349727 A      5/2002
CN      200942153 Y      9/2007
(Continued)

OTHER PUBLICATIONS

Weisz et. al. "Tinnitus Perception and Distress Is Related to Abnormal Spontaneous Brain Activity as Measured by Magnetoencephalography" published Jun. 25, 2005 by PLoS Medicine retrieved from: https://www.ncbi.nlm.nih.gov/pmc/articles/PMC1160568/, pp. 1-8 (Year: 2005).*
(Continued)

*Primary Examiner* — Devin B Henson
*Assistant Examiner* — Matthew Eric Ogles
(74) *Attorney, Agent, or Firm* — Knobbe, Martens, Olson & Bear, LLP (57) ABSTRACT

A method is provided which includes receiving first signals indicative of sound in an environment of a recipient. The method further includes receiving second signals indicative of sound perception by the recipient. The method further includes, in response to the first signals and the second signals, determining whether the recipient is experiencing tinnitus. The method further includes, while the recipient is experiencing tinnitus, transmitting stimulation signals to the auditory system of the recipient.

23 Claims, 9 Drawing Sheets

(51) Int. Cl.
*A61B 5/372* (2021.01)
*A61B 5/38* (2021.01)
*A61F 11/00* (2022.01)
*G16H 20/30* (2018.01)
*H04R 25/00* (2006.01)

(52) U.S. Cl.
CPC ............. *A61F 11/00* (2013.01); *G16H 20/30* (2018.01); *H04R 25/75* (2013.01)

(56) References Cited

U.S. PATENT DOCUMENTS

| | | | |
|---|---|---|---|
| 7,010,354 | B1 | 3/2006 | Grayden et al. |
| 7,572,234 | B2 | 8/2009 | Viirre et al. |
| 8,666,099 | B2 | 3/2014 | Nielsen et al. |
| 8,888,712 | B2 | 3/2014 | Nielsen et al. |
| 2004/0066944 | A1* | 4/2004 | Leenen ................ H04R 25/305 381/314 |
| 2005/0043646 | A1* | 2/2005 | Viirre .................... A61B 5/375 600/544 |
| 2007/0183604 | A1 | 8/2007 | Araki et al. |
| 2009/0163828 | A1* | 6/2009 | Turner .................... A61B 5/38 600/559 |
| 2012/0203130 | A1 | 8/2012 | Armin |
| 2012/0253104 | A1* | 10/2012 | Andersson ........... H04R 25/606 600/25 |
| 2013/0131542 | A1 | 5/2013 | Henry et al. |
| 2014/0148724 | A1* | 5/2014 | Ungstrup ................ A61B 5/121 600/25 |
| 2014/0254808 | A1 | 9/2014 | Park et al. |
| 2015/0018699 | A1 | 1/2015 | Zeng et al. |
| 2016/0277852 | A1* | 9/2016 | Lee ..................... H04R 25/405 |
| 2017/0071534 | A1 | 3/2017 | Zhao et al. |
| 2017/0164121 | A1* | 6/2017 | Herscher .............. H04R 25/402 |
| 2017/0347213 | A1* | 11/2017 | Goorevich .......... H04R 25/505 |
| 2017/0365101 | A1* | 12/2017 | Samec ................. G06T 19/006 |
| 2018/0271710 | A1* | 9/2018 | Boesen ................ A61B 5/7203 |

FOREIGN PATENT DOCUMENTS

| | | |
|---|---|---|
| CN | 101939041 A | 1/2011 |
| CN | 102075842 A | 5/2011 |
| CN | 102370542 A | 3/2012 |
| CN | 105686902 A | 6/2016 |
| WO | WO 2011/127930 | 10/2011 |

OTHER PUBLICATIONS

M. Meyer et al., "Disentangling Tinnitus Distress and Tinnitus Presence by Means of EEG Power Analysis," Neural Plasticity, vol. 2014, Article ID 468546, 13 pages, http://dx.doi.org/10.1155/2014/468546 (2014).

E. van der Loo et al., "Tinnitus Intensity Dependent Gamma Oscillations of the Contralateral Auditory Cortex," PLoS One 4(10): e7396, doi: 10.1371/journal.pone.0007396 (2009).

S. Vanneste and D. De Ridder, "The auditory and non-auditory brain areas involved in tinnitus. An emergent property of multiple parallel overlapping subnetworks," Frontiers in Sys. Neuroscience, vol. 6, Article 31, doi: 10.3389/fnsys.2012.00031 (2012).

International Search Report and Written Opinion in PCT Application No. PCT/IB2020/052172 dated Jun. 29, 2020 in 14 pages.

* cited by examiner

SYSTEM AND METHOD FOR TINNITUS SUPPRESSION

BACKGROUND

Field

The present application relates generally to a prosthesis configured to suppress the effects of tinnitus on a recipient of the auditory prosthesis.

Description of the Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain. Auditory prostheses of various types are widely used to improve the lives of users. Such devices include, for example, hearing aids, cochlear implants, bone conduction implants, middle ear implants, and electro-acoustic devices.

Individuals who suffer from conductive hearing loss typically have some form of residual hearing because the hair cells in the cochlea are undamaged. As a result, individuals suffering from conductive hearing loss might receive an auditory prosthesis that generates mechanical motion of the cochlea fluid instead of a hearing aid based on the type of conductive loss, amount of hearing loss and customer preference. Such prostheses include, for example, bone conduction devices and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical, and the like). Cochlear implants are often proposed when the sensorineural hearing loss is due to the absence or destruction of the cochlea hair cells, which transduce acoustic signals into nerve impulses. Auditory brainstem stimulators might also be proposed when a recipient experiences sensorineural hearing loss due to damage to the auditory nerve.

Forms of these auditory prostheses which are "mostly implantable," "fully implantable," or "totally implantable" have the advantage of allowing the user to have a superior aesthetic result, as the recipient is visually indistinguishable in day-to-day activities from individuals that have not received such devices. Such devices also have a further advantage in generally being inherently waterproof, allowing the recipient to shower, swim, and so forth without needing to take any special measures. Examples of such devices include, but are not limited to, totally implanted cochlear implants ("TICIs"), mostly implantable cochlear implants ("MICI"), and fully implantable middle ear implants utilizing totally implantable actuators ("TIAs").

SUMMARY

In one aspect disclosed herein, a method is provided which comprises receiving first signals indicative of sound in an environment of a recipient. The method further comprises receiving second signals indicative of sound perception by the recipient. The method further comprises, in response to the first signals and the second signals, determining whether the recipient is experiencing tinnitus. In certain embodiments, the method further comprises, while the recipient is experiencing tinnitus, transmitting stimulation signals to the auditory system of the recipient.

In another aspect disclosed herein, an apparatus is provided which comprises control circuitry configured to receive sensor signals indicative of a biological response of a recipient. The biological response is associated with phantom sound perception by the recipient. The control circuitry is further configured to generate control signals in response at least in part to the sensor signals. The apparatus further comprises signal processing circuitry configured to generate data signals in response at least in part to the control signals. The signal processing circuitry is further configured to transmit the data signals to an actuating assembly of an auditory prosthesis.

In still another aspect disclosed herein, an apparatus is provided which comprises signal processing circuitry configured to receive transducer signals indicative of sound received by at least one acoustic transducer worn or implanted within a recipient and to generate data signals to be provided to at least one actuating assembly of an auditory prosthesis worn or implanted within the recipient. The apparatus further comprises control circuitry configured to monitor a neural response of the recipient and the transducer signals, the data signals, or both the transducer signals and the data signals. The control circuitry is further configured to generate control signals indicative of a masking contribution to be included in the data signals, the masking contribution configured to at least partially mask tinnitus being experienced by the recipient.

BRIEF DESCRIPTION OF THE DRAWINGS

Embodiments are described herein in conjunction with the accompanying drawings, in which.

DETAILED DESCRIPTION

Tinnitus is an auditory phantom process, which may be perceived as having various characteristics (e.g., pure tone; narrow band noise; polyphonic) and experienced either unilaterally or bilaterally. A recipient perceiving tinnitus can experience biological effects that can be detected and/or measured. For example, animal experiments have demonstrated that the degree of behavioral importance of an external sound is related to the representational expansion of its frequency in the primary auditory cortex. In addition, there is a sound level dependent activation in the gamma band of the contralateral auditory cortex which, while likely not related to the tinnitus perception per se, codes for its perceived intensity. Furthermore, while the tinnitus percept has been reported in association with the gamma band, there is a relationship between the strength of distress and neural modulations in the upper beta band as well. Thus, the presence of a phantom auditory presentation can be identified, detected, and/or characterized (e.g., intensity or magnitude of the phantom auditory presentation) using electroencephalograph (EEG) measurements.

Masking has previously been used to treat tinnitus, with either audible or electrical stimulation at a consistent level. Masking can comprise adding a masking stimulus (e.g., signals) corresponding to sound (e.g., white noise; music; patterned sound; low-level sound; sound tailored based on characteristics of the recipient's tinnitus) to the sound from the ambient auditory environment in order to mask or cover up the phantom sound (e.g., ringing; hissing) due to tinnitus. The added sound level can be close to or louder than the perceived loudness of the phantom sound. While the tinnitus can be partially or fully masked by the added sound such that the recipient's perception of the phantom sound is reduced, masking does not reduce or eliminate the tinnitus itself. In a loud auditory environment, masking may be easily achieved, but in more quiet auditory environments, the consistent level of auditory stimulation used in masking may be undesirable. In addition, in some cases, the perception of tinnitus is intermittent or variable in magnitude.

Certain embodiments described herein advantageously provide an automated system and method for adjusting the masking stimulus (e.g., modifying an amplitude-frequency distribution, timing profile, duty cycle, and/or spectral content of the masking stimulus; increasing and/or decreasing a magnitude of the masking stimulus; activating and/or deactivating the masking stimulus) without intervention by the recipient and/or medical professional (e.g., in a hands-off manner). By monitoring one or more predetermined biomarkers (e.g., predetermined characteristics of EEG measurements) indicative of the presence, intensity, and/or other characteristics of auditory phantoms and responding by adjusting the masking stimulus, certain embodiments advantageously provide an automated technique for treating tinnitus (e.g., using an active, closed loop configuration). For example, the masking stimulus can be delivered to the recipient (i) only when an auditory phantom is detected, (ii) at an appropriate level to only just suppress the auditory phantom, (iii) only when the auditory phantom is causing distress, (iv) in a manner to de-emphasize pulsatile tinnitus, and/or (v) moderated by the level of distress experienced by the recipient.

Figure 1:
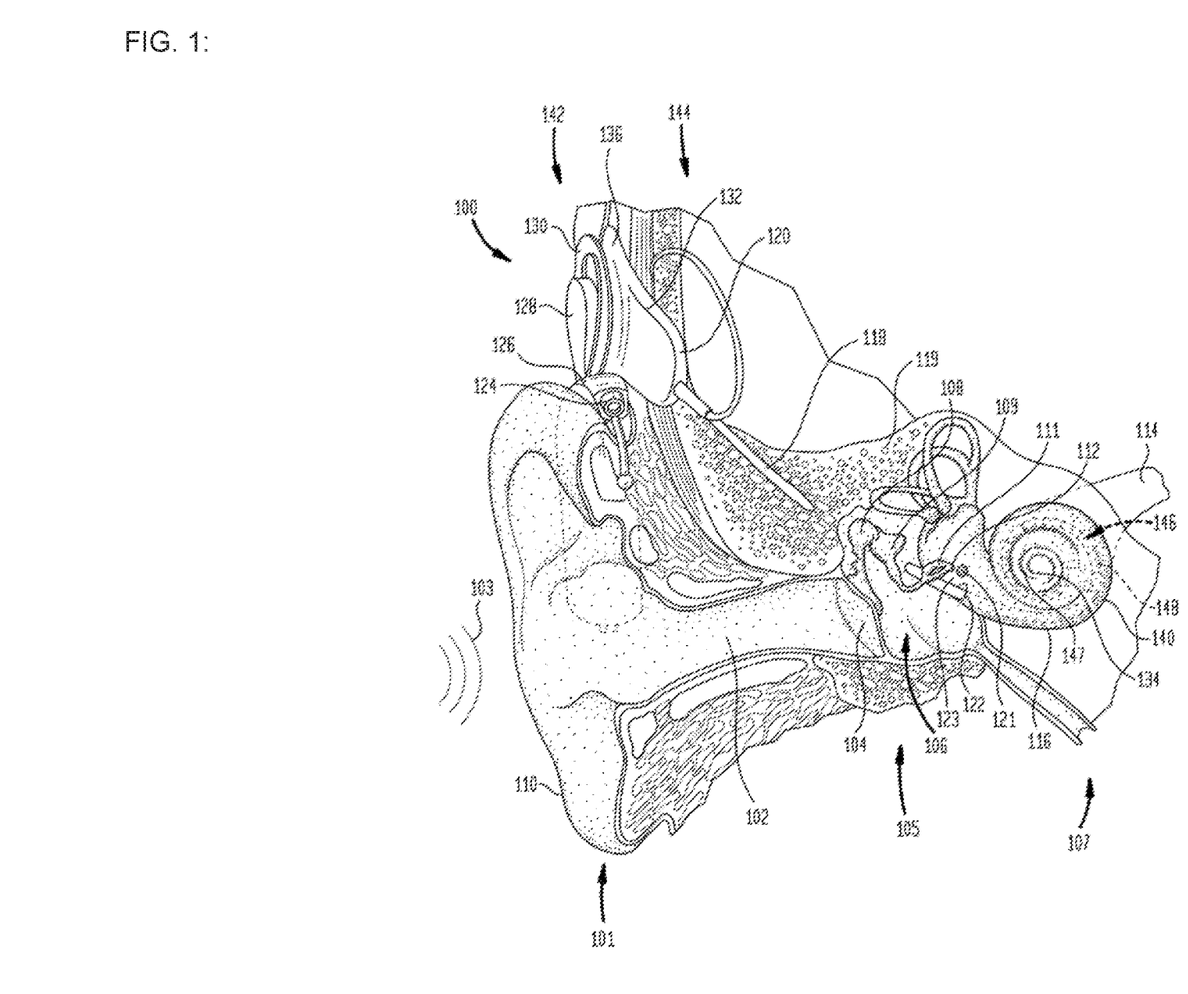
FIG. 1 is a perspective view of an example cochlear implant auditory prosthesis implanted in a recipient in accordance with certain embodiments described herein.

FIG. 1 is a perspective view of an example cochlear implant auditory prosthesis 100 implanted in a recipient in accordance with certain embodiments described herein. The example auditory prosthesis 100 is shown in FIG. 1 as comprising an implanted stimulator unit 120 (e.g., an actuator) and an external microphone assembly 124 (e.g., a partially implantable cochlear implant). An example auditory prosthesis 100 (e.g., a mostly, fully, or totally implantable cochlear implant) in accordance with certain embodiments described herein can replace the externally disposed microphone assembly 124 shown in FIG. 1 with a subcutaneously implantable assembly comprising an acoustic transducer (e.g., microphone). Such microphone assemblies are configured to be positioned (e.g., in a surgical procedure) beneath the skin and on, within, or proximate to the recipient's skull and at a location that facilitates the receipt of acoustic signals by the microphone assembly once implanted (e.g., at a location between the recipient's skin and skull, rearward and upward of the recipient's ear or in the mastoid region).

As shown in FIG. 1, the recipient has an outer ear 101, a middle ear 105, and an inner ear 107. In a fully functional ear, the outer ear 101 comprises an auricle 110 and an ear canal 102. An acoustic pressure or sound wave 103 is collected by the auricle 110 and is channeled into and through the ear canal 102. Disposed across the distal end of the ear canal 102 is a tympanic membrane 104 which vibrates in response to the sound wave 103. This vibration is coupled to oval window or fenestra ovalis 112 through three bones of middle ear 105, collectively referred to as the ossicles 106 and comprising the malleus 108, the incus 109, and the stapes 111. The bones 108, 109, and 111 of the middle ear 105 serve to filter and amplify the sound wave 103, causing the oval window 112 to articulate, or vibrate in response to vibration of the tympanic membrane 104. This vibration sets up waves of fluid motion of the perilymph within cochlea 140. Such fluid motion, in turn, activates tiny hair cells (not shown) inside the cochlea 140. Activation of the hair cells causes appropriate nerve impulses to be generated and transferred through the spiral ganglion cells (not shown) and auditory nerve 114 to the brain (also not shown) where they are perceived as sound.

As shown in FIG. 1, the example auditory prosthesis 100 comprises one or more components which are temporarily or permanently implanted in the recipient. The example auditory prosthesis 100 is shown in FIG. 1 with an external component 142 which is directly or indirectly attached to the recipient's body, and an internal component 144 which is temporarily or permanently implanted in the recipient (e.g., positioned in a recess of the temporal bone adjacent auricle 110 of the recipient). The external component 142 typically comprises one or more sound input elements (e.g., an external microphone 124) for detecting sound, a sound processing unit 126 (e.g., disposed in a Behind-The-Ear unit), a power source (not shown), and an external transmitter unit 128. In the illustrative embodiments of FIG. 1, the external transmitter unit 128 comprises an external coil 130 (e.g., a wire antenna coil comprising multiple turns of electrically insulated single-strand or multi-strand platinum or gold wire) and, preferably, a magnet (not shown) secured directly or indirectly to the external coil 130. The external coil 130 of the external transmitter unit 128 is part of an inductive radio frequency (RF) communication link with the internal component 144. The sound processing unit 126 processes the output of the microphone 124 that is positioned externally to the recipient's body, in the depicted embodiment, by the recipient's auricle 110. The sound processing unit 126 generates encoded signals, sometimes referred to herein as encoded data signals, which are provided to the external transmitter unit 128 (e.g., via a cable). As will be appreciated, the sound processing unit 126 can utilize digital processing techniques to provide frequency shaping, amplification, compression, and other signal conditioning, including conditioning based on recipient-specific fitting parameters.

The power source of the external component 142 is configured to provide power to the auditory prosthesis 100, where the auditory prosthesis 100 includes a battery (e.g., located in the internal component 144, or disposed in a separate implanted location) that is recharged by the power provided from the external component 142 (e.g., via a transcutaneous energy transfer link). The transcutaneous energy transfer link is used to transfer power and/or data to the internal component 144 of the auditory prosthesis 100. Various types of energy transfer, such as infrared (IR), electromagnetic, capacitive, and inductive transfer, may be used to transfer the power and/or data from the external component 142 to the internal component 144. During operation of the auditory prosthesis 100, the power stored by the rechargeable battery is distributed to the various other implanted components as needed.

The internal component 144 comprises an internal receiver unit 132, a stimulator unit 120, and an elongate electrode assembly 118. In some embodiments, the internal receiver unit 132 and the stimulator unit 120 are hermetically sealed within a biocompatible housing. The internal receiver unit 132 comprises an internal coil 136 (e.g., a wire antenna coil comprising multiple turns of electrically insulated single-strand or multi-strand platinum or gold wire), and preferably, a magnet (also not shown) fixed relative to the internal coil 136. The internal receiver unit 132 and the stimulator unit 120 are hermetically sealed within a biocompatible housing, sometimes collectively referred to as a stimulator/receiver unit. The internal coil 136 receives power and/or data signals from the external coil 130 via a transcutaneous energy transfer link (e.g., an inductive RF link). The stimulator unit 120 generates electrical stimulation signals based on the data signals, and the stimulation signals are delivered to the recipient via the elongate electrode assembly 118.

The elongate electrode assembly 118 has a proximal end connected to the stimulator unit 120, and a distal end implanted in the cochlea 140. The electrode assembly 118 extends from the stimulator unit 120 to the cochlea 140 through the mastoid bone 119. In some embodiments, the electrode assembly 118 may be implanted at least in the basal region 116, and sometimes further. For example, the electrode assembly 118 may extend towards apical end of cochlea 140, referred to as cochlea apex 134. In certain circumstances, the electrode assembly 118 may be inserted into the cochlea 140 via a cochleostomy 122. In other circumstances, a cochleostomy may be formed through the round window 121, the oval window 112, the promontory 123, or through an apical turn 147 of the cochlea 140.

The elongate electrode assembly 118 comprises a longitudinally aligned and distally extending array 146 of electrodes or contacts 148, sometimes referred to as electrode or contact array 146 herein, disposed along a length thereof. Although the electrode array 146 can be disposed on the electrode assembly 118, in most practical applications, the electrode array 146 is integrated into the electrode assembly 118 (e.g., the electrode array 146 is disposed in the electrode assembly 118). As noted, the stimulator unit 120 generates stimulation signals which are applied by the electrodes 148 to the cochlea 140, thereby stimulating the auditory nerve 114.

While FIG. 1 schematically illustrates an auditory prosthesis 100 utilizing an external component 142 comprising an external microphone 124, an external sound processing unit 126, and an external power source, in certain other embodiments, one or more of the microphone 124, sound processing unit 126, and power source are implantable on or within the recipient (e.g., within the internal component 144). For example, the auditory prosthesis 100 can have each of the microphone 124, sound processing unit 126, and power source implantable on or within the recipient (e.g., encapsulated within a biocompatible assembly located subcutaneously), and can be referred to as a totally implantable cochlear implant ("TICI"). For another example, the auditory prosthesis 100 can have most components of the cochlear implant (e.g., excluding the microphone, which can be an in-the-ear-canal microphone) implantable on or within the recipient, and can be referred to as a mostly implantable cochlear implant ("MICI").

Figure 2A:
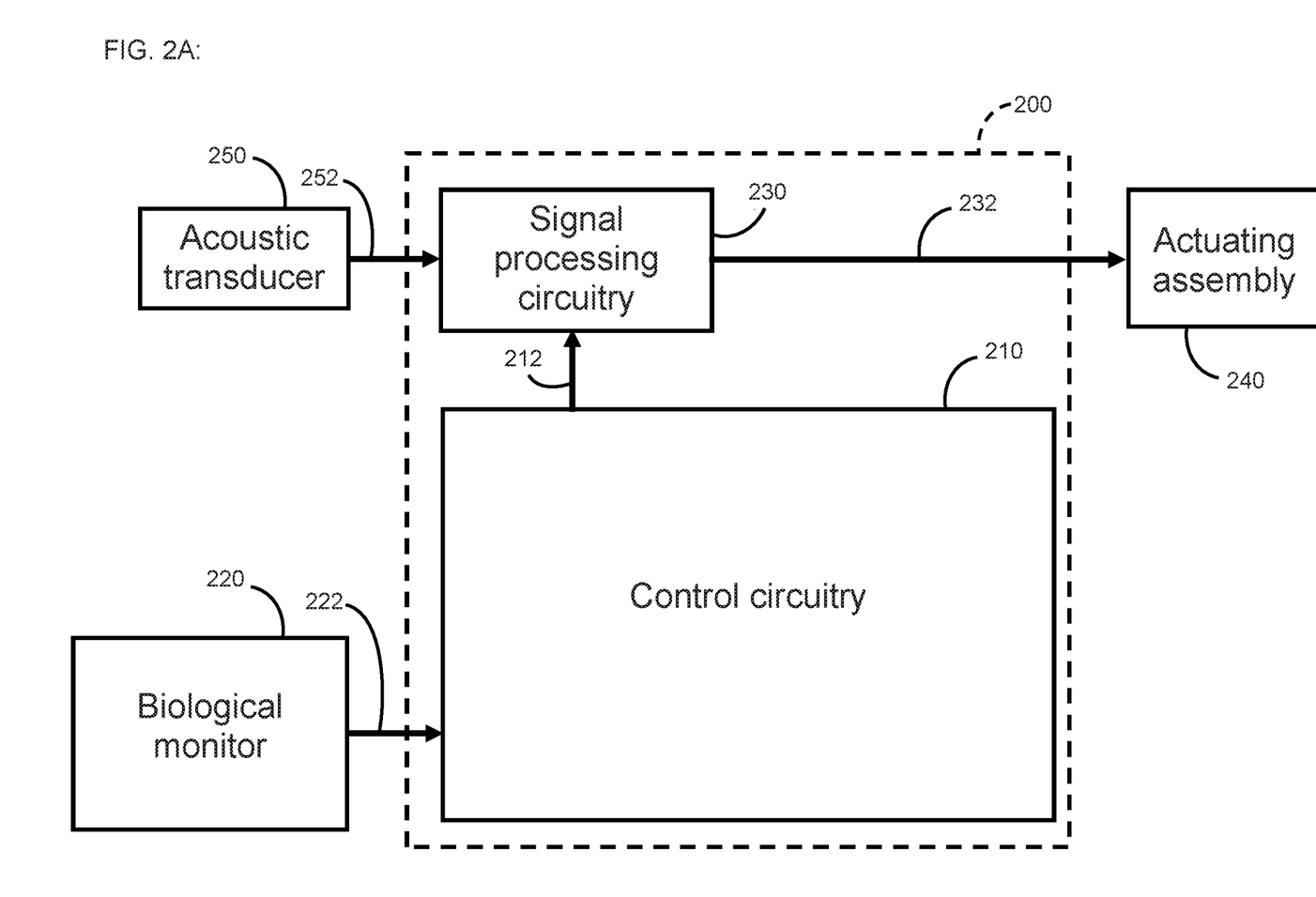
FIGS. 2A and 2B schematically illustrate an example apparatus in accordance with certain embodiments described herein.
Figure 2B:
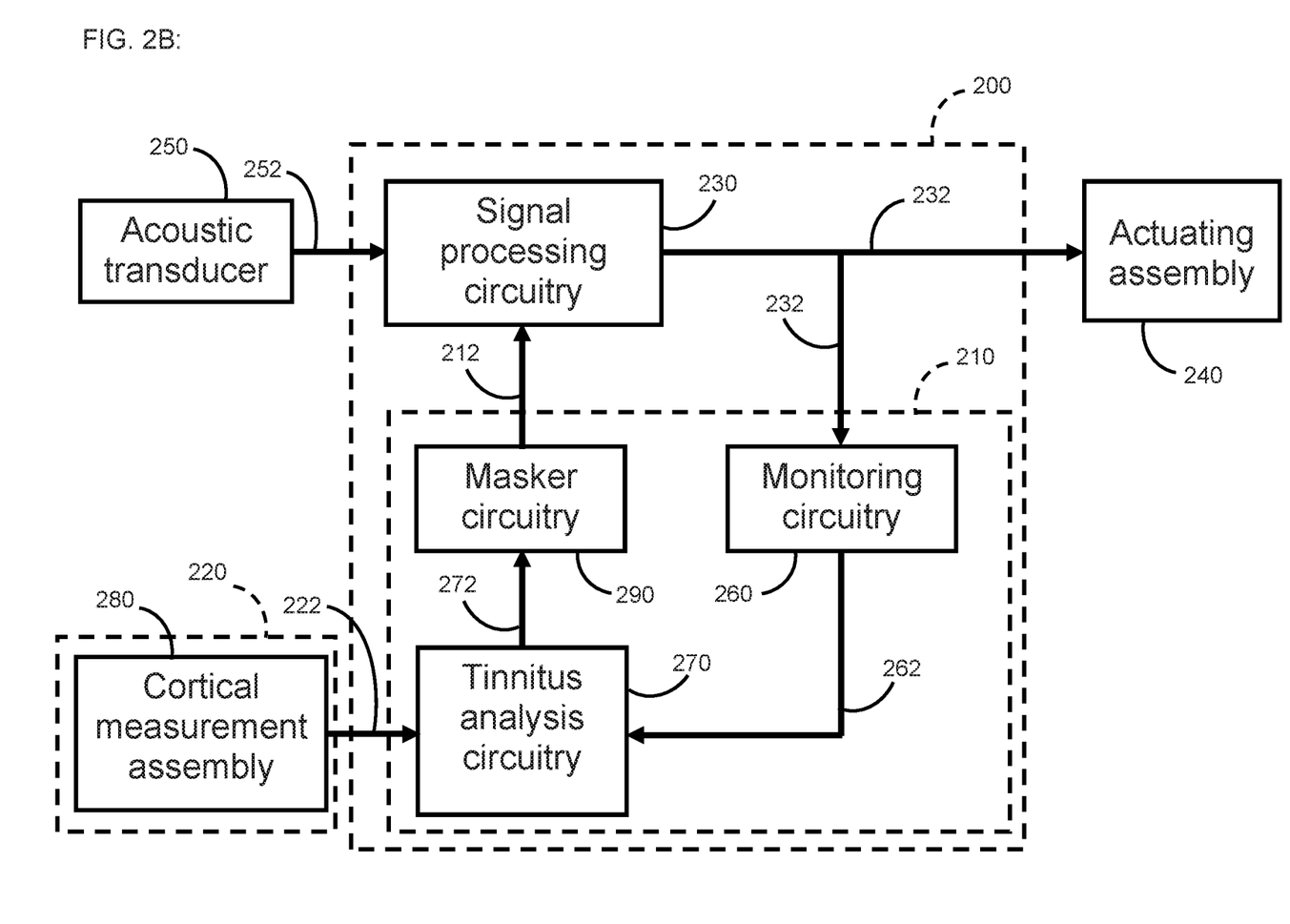

FIGS. 2A and 2B schematically illustrate an example apparatus 200 in accordance with certain embodiments described herein. By monitoring one or more predetermined biomarkers (e.g., predetermined characteristics of EEG measurements) indicative of the presence, intensity, and/or other characteristics of auditory phantoms and responding (e.g., by adjusting a masking stimulus), the example apparatus 200 of certain embodiments is configured to treat tinnitus. For example, the apparatus 200 can be configured to automatically and actively adjust a masking stimulus (e.g., modify an amplitude-frequency distribution, timing profile, duty cycle, and/or spectral content of the masking stimulus; increase and/or decrease a magnitude of the masking stimulus; activate and/or deactivate the masking stimulus) without intervention by the recipient and/or medical professional (e.g., in a hands-off manner) in a closed loop configuration. For other examples, the apparatus 200 can be configured to initiate (e.g., trigger) other therapeutic and/or tinnitus-suppressing actions (e.g., deliver therapeutic medication; apply nerve stimulation, such as to the vagus nerve), to communicate the detected existence of the one or more predetermined biomarkers to an assembly configured to perform other therapeutic and/or tinnitus-suppressing actions (e.g., deliver therapeutic medication; apply nerve stimulation, such as to the vagus nerve), and/or to communicate the detected existence of the one or more predetermined biomarkers to a medical professional (e.g., caregiver).

In certain embodiments, the apparatus 200 is a component of an implantable (e.g., fully implantable or partially implantable) or non-implantable auditory prosthesis system, examples of which include but are not limited to: a cochlear implant system, a bone conduction implant system (e.g., active bone conduction system; passive bone conduction system, percutaneous bone conduction system; transcutaneous bone conduction system), a hearing aid system, a Direct Acoustic Cochlear Implant (DACI) system, a middle ear implant system, a middle ear transducer (MET) system, an electro-acoustic implant system, another type of auditory prosthesis system, and/or combinations or variations thereof, or any other suitable hearing prosthesis system with or without one or more external components. For example, U.S. Pat. Appl. Publ. No. 2017/0347213 discloses a tinnitus relief system combined with a cochlear implant system compatible with certain embodiments described herein.

Embodiments can include any type of auditory prosthesis that can utilize the teachings detailed herein and/or variations thereof.

The apparatus 200 of FIGS. 2A and 2B comprises control circuitry 210 (e.g., firmware, software, or a combination of both firmware and software) configured to receive (e.g., from a biological monitor 220) sensor signals 222 indicative of a biological response (e.g., a predetermined biomarker) of a recipient. The biological response is associated with phantom sound perception by the recipient. The control circuitry 210 is further configured to generate control signals 212 in response at least in part to the sensor signals 222. The apparatus 200 further comprises signal processing circuitry 230 configured to generate data signals 232 in response at least in part to the control signals 212 and to transmit the data signals 232 to an actuating assembly 240 of an auditory prosthesis (e.g., an implanted stimulator unit 120 of a cochlear implant auditory prosthesis 100). In certain embodiments, as schematically illustrated by FIG. 2B, the control circuitry 210 comprises monitoring circuitry 260, tinnitus analysis circuitry 270 (e.g., configured to be operatively coupled to a cortical measurement assembly 280 of the biological monitor 220), and masker circuitry 290.

As described herein, by comparing the sensor signals 222 indicative of the biological response of the recipient to signals indicative of actual sounds received by an acoustic transducer 250 worn by the recipient, the control circuitry 210 of certain embodiments is configured to objectively measure tinnitus onset and to tailor the masking signals provided to the recipient to automatically counteract (e.g., reduce) the effects of the tinnitus. For example, as schematically illustrated in FIG. 2B, the control circuitry 210 is configured to provide an active, automated, closed-loop suppression of the effects of tinnitus (e.g., masking as needed, when needed, and at a minimum viable intensity level, without user intervention). In certain embodiments, the control circuitry 210 is further configured to preemptively counteract the effects of tinnitus even before the recipient perceives the phantom sounds (e.g., before the phantom sounds have become loud enough for the recipient to become consciously aware of the phantom sounds) and/or before the recipient suffers discomfort as a result of the phantom sounds.

As schematically illustrated in FIGS. 2A and 2B, the apparatus 200 can be further configured to be operatively coupled to at least one acoustic transducer 250 (e.g., at least one microphone). The at least one acoustic transducer 250 is configured to respond to sound received by the at least one acoustic transducer 250 by generating transducer signals 252 indicative of the sound received by the at least one acoustic transducer 250 and transmitting the transducer signals 252 to the apparatus 200 (e.g., the signal processing circuitry 230). In certain embodiments, the at least one acoustic transducer 250 includes one or more microphone assemblies that are positioned externally to the recipient and/or one or more microphone assemblies that are implanted on or within the recipient. The teachings detailed herein and/or variations thereof can be utilized with any type of external or implantable microphone arrangement.

In certain embodiments, the apparatus 200 comprises a signal processing unit (e.g., external or implantable) of an auditory prosthesis system (e.g., auditory prosthesis 100) which can comprise the signal processing circuitry 230 and/or at least a portion of the control circuitry 210. For example, the signal processing unit can comprise a digital signal processor ("DSP") having one or more microprocessors or application-specific integrated circuits ("ASICs") which comprise one or more portions of the control circuitry 210 (e.g., one or more of the monitoring circuitry 260, tinnitus analysis circuitry 270, and masker circuitry 290) and the signal processing circuitry 230. In certain embodiments, the control circuitry 210 (e.g., one or more of the monitoring circuitry 260, tinnitus analysis circuitry 270, and masker circuitry 290) and/or the signal processing circuitry 230 comprises at least one processor (e.g., microelectronic circuitry; one or more microprocessors or ASICs) and at least one storage device (e.g., non-volatile memory; flash memory) operatively coupled to the at least one processor. In certain embodiments, two or more of the monitoring circuitry 260, tinnitus analysis circuitry 270, and masker circuitry 290 comprise the same at least one processor and/or the same at least one storage device. In certain embodiments, the control circuitry 210 and the signal processing circuitry 230 comprise the same at least one processor and/or the same at least one storage device. While the monitoring circuitry 260, tinnitus analysis circuitry 270, and masker circuitry 290 are described herein as being separate components in communication with one another (e.g., via monitoring signals 262 and detection signals 272), in certain embodiments, two or more of these portions of the control circuitry 210 are integrated with one another and providing the functionality described herein without transmitting at least some of the signals (e.g., monitoring signals 262 and detection signals 272) therebetween.

In certain embodiments, the signal processing circuitry 230 is configured to generate the data signals 232 in response at least in part to the transducer signals 252. The signal processing circuitry 230 of certain embodiments comprises filtering circuitry and an automatic gain controller (AGC) configured to apply filtering (e.g., adaptive filtering) to the resultant data signals 232. For example, the filtering circuitry can be configured to generate filtering signals indicative of artifacts, noise, oscillations, instabilities and/or other unwanted acoustic effects of the transducer signals 252, and the AGC can be configured to generate and apply corrections to reduce these unwanted effects in the data signals 232.

In certain embodiments, the actuating assembly 240 is configured to receive and respond to the data signals 232 by generating and providing stimulation signals to the auditory system of the recipient. For example, for a cochlear implant auditory prosthesis, the actuating assembly 240 can comprise a stimulation unit 120 having an elongate electrode assembly 118 with an array 146 of electrodes 148, disposed along a length thereof and configured to apply the stimulation signals to the cochlea 140, thereby stimulating the auditory nerve 114.

In certain embodiments, the monitoring circuitry 260 is configured to receive and monitor the data signals 232 from the signal processing circuitry 230. In certain other embodiments, the monitoring circuitry 260 is configured to receive and monitor the transducer signals 252 from the at least one acoustic transducer 250. In certain other embodiments, the monitoring circuitry 260 is configured to receive and monitor the data signals 232 and the transducer signals 252. The monitoring circuitry 260 of certain embodiments is configured to monitor the data signals 232 and/or transducer signals 252 for one or more characteristics (e.g., amplitude, frequency, spectral content, and/or noise level) of the auditory environment and/or for changes of the one or more characteristics that are of sufficient degree (e.g., satisfying at least one predetermined condition with respect to at least one predetermined range) to warrant determining whether tinnitus is being perceived by the recipient (e.g., determining whether tinnitus is present). For example, the monitoring circuitry 260 can be configured to detect whether the auditory environment is sufficiently loud (e.g., sound levels above a predetermined value) such that the recipient is likely not perceiving any auditory phantoms to a degree warranting masking by the apparatus 200 and/or to detect whether the auditory environment is sufficiently quiet (e.g., sound levels below a predetermined value) such that the recipient is potentially perceiving an auditory phantom to a degree warranting masking by the apparatus 200.

The monitoring circuitry 260 of certain embodiments is further configured to generate and transmit the monitoring signals 262 to the tinnitus analysis circuitry 270. In certain embodiments, the monitoring signals 262 include information regarding the detected characteristics of the auditory environment and/or the detected changes of the characteristics which are indicative of potential tinnitus perception by the recipient.

In certain embodiments, the tinnitus analysis circuitry 270 is in operable communication with the biological monitor 220 and configured to receive the sensor signals 222 from the biological monitor 220. The tinnitus analysis circuitry 270 of certain embodiments is configured to transmit a triggering signal to the biological monitor 220 (e.g., to initiate measurements of the biological response of the recipient by the biological monitor 220) upon the monitoring signals 262 indicating that the recipient is potentially perceiving an auditory phantom. In certain embodiments, the tinnitus analysis circuitry 270 is further configured to receive and respond to the monitoring signals 262 by analyzing the sensor signals 222 to determine whether the recipient is perceiving auditory phantoms (e.g., due to tinnitus).

In certain embodiments, the biological monitor 220 comprises a cortical measurement assembly 280 configured to perform electroencephalograph (EEG) measurements and to transmit the sensor signals 222 (e.g., EEG signals indicative of a neural response of the recipient) to the tinnitus analysis circuitry 270. For example, the EEG measurements can be independent of, or interleaved with, stimulation by the actuating assembly 240 and can be used to identify the onset of tinnitus, magnitude of tinnitus, and/or level of distress caused by tinnitus. In certain embodiments, the EEG measurements are performed by the cortical measurement assembly 280 using one or more electrodes configured to be responsive to electrical activity of the recipient's brain. The cortical measurement assembly 280 of certain embodiments is configured to detect electrical potentials (e.g., spontaneous electrical potentials; evoked electrical potentials correlated with stimulus presentation) between at least two electrodes responsive to the brain electrical activity. The at least two electrodes can be selected from the group consisting of: an implanted extra-cochlear electrode (e.g., a sub-dermal electrode); an implanted intra-cochlear electrode; an electrode on the recipient's skin surface. For example, the EEG electric potentials can be measured between two or more implanted extra-cochlear electrodes, between two or more electrodes on the skin surface of the recipient, between one or more implanted extra-cochlear electrodes and one or more electrodes on the recipient's skin surface, between one or more implanted extra-cochlear electrodes and one or more implanted intra-cochlear electrodes (e.g., one or more electrodes 148 of the electrode array 146 of the elongate electrode assembly 118; see, e.g., U.S. Pat. Appl. Publ. No. 2015/0018699A1).

In certain embodiments, the tinnitus analysis circuitry 270 is configured to use the EEG measurements to detect the presence of tinnitus. For example, at least some of the cortical responses (e.g., mismatch negativity (MMN) responses and/or P100 responses) to auditory stimuli tend to be suppressed for people experiencing tinnitus as compared to such cortical responses for people with normal hearing. Without being bound by theory, the presence of tinnitus can make the auditory stimuli less noticeable by the recipient, leading to weakened responses at the cortical level.

Figure 3:
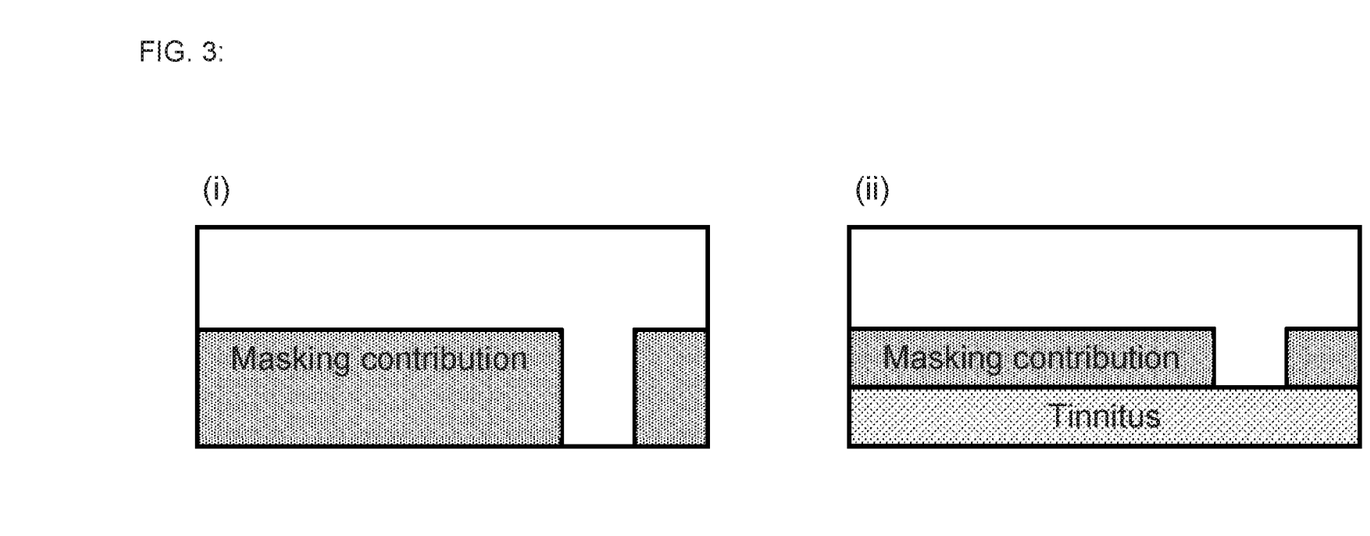
FIG. 3 schematically illustrates an example change of a masking contribution of the data signals (i) in the absence of tinnitus and (ii) in the presence of tinnitus.

In certain embodiments, the cortical measurement assembly 280 is configured to measure auditory evoked potentials (e.g., potentials correlated with auditory stimuli) to be used by the tinnitus analysis circuitry 270 to detect the presence of tinnitus. In certain such embodiments, the auditory stimuli are generated by the signal processing circuitry 230 in response to the control signals 212 from the control circuitry 210. For example, the control signals 212 can instruct the signal processing circuitry 230 to change a masking contribution of the data signals 232, thereby resulting in a corresponding change in the stimulation signals generated by the actuating assembly 240 and provided to the recipient's auditory system. FIG. 3 schematically illustrates an example change of a masking contribution of the data signals 232 (i) in the absence of tinnitus and (ii) in the presence of tinnitus. The change comprises introducing a gap (e.g., a relatively short time period during which the masking contribution is reduced or zero) in an otherwise constant masking contribution. As schematically illustrated by FIG. 3, the presence of tinnitus reduces the magnitude of the MMN response due to the gap as compared to the MMN response magnitude due to the gap in the absence of tinnitus. In certain embodiments, other changes of the masking contribution (e.g., changes in the masking spectral components; changes in the masking volume) are used as the auditory stimuli presented to the recipient.

In certain embodiments, the tinnitus analysis circuitry 270 is further configured to respond to monitoring signals 262 (e.g., indicative of auditory stimuli being provided to the recipient; indicative of changes to the auditory environment) by triggering the biological monitor 220 (e.g., the cortical measurement assembly 280) to generate the sensor signals 222 (e.g., one or more cortical measurements) and to provide the sensor signals 222 to the tinnitus analysis circuitry 270. For example, upon the monitoring circuitry 260 detecting the auditory stimuli or auditory environment changes (e.g., as expressed in the data signals 232), the monitoring signals 262 can be indicative of the auditory stimuli or the auditory environment changes, and the tinnitus analysis circuitry 270 can provide a trigger signal to the cortical measurement assembly 280 to initiate the one or more cortical measurements.

In certain embodiments, the tinnitus analysis circuitry 270 is further configured to respond to the monitoring signals 262 (e.g., indicative of the auditory stimuli and/or the auditory environment changes) and to respond to the sensor signals 222 (e.g., indicative of the neural response of the recipient) by generating detection signals 272 indicative of the presence or absence of tinnitus (e.g., whether the recipient is experiencing tinnitus; whether the recipient is perceiving phantom sounds that are not from the auditory environment). In certain embodiments, the detection signals 272 further include information regarding one or more characteristics (e.g., magnitude) of the tinnitus.

In certain embodiments, the masker circuitry 290 is configured to receive the detection signals 272 and, in response at least in part to the detection signals 272, to generate the control signals 212 which are transmitted to the signal processing circuitry 230. In certain embodiments, the control signals 212 are indicative of a masking contribution to the data signals 232 (e.g., indicative of modifications to the masking contribution) to be made by the signal processing circuitry 230. The masking contribution of certain embodiments is configured to at least partially mask or otherwise counteract the effects of tinnitus being experienced by the recipient (e.g., the level of the masking signal can be close to or louder than the perceived loudness of the phantom sound). The data signals 232, including the masking contributions, are transmitted to the actuating assembly 240, which is configured to transmit stimulation signals to the auditory system of the recipient. The stimulation signals are configured to at least partially alleviate (e.g., mask) phantom-sound-based discomfort of the recipient (e.g., to at least partially mask the phantom sound perception by the recipient; to at least partially reduce the effects of tinnitus being experienced by the recipient).

FIGS. 4-8 are flow diagrams of various example methods in accordance with certain embodiments described herein. While the example methods of FIGS. 4-8 are described by reference to the example apparatus of FIGS. 2A and 2B, the example methods of FIGS. 4-8 can be performed by other structures in accordance with certain embodiments described herein. In certain embodiments, only one of the example methods of FIGS. 4-8 is used, while in certain other embodiments, two or more of the example methods are used in combination with one another.

Figure 4A:
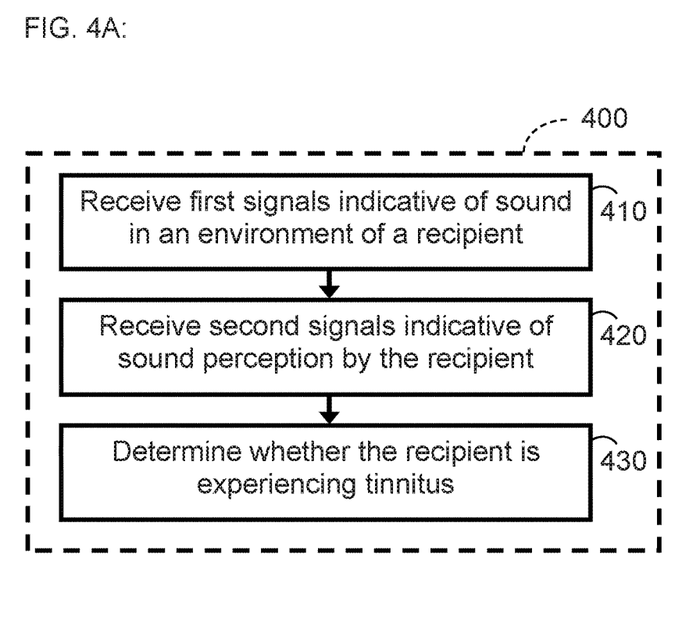
FIGS. 4A and 4B are flow diagrams of two example methods in accordance with certain embodiments described herein.
Figure 4B:
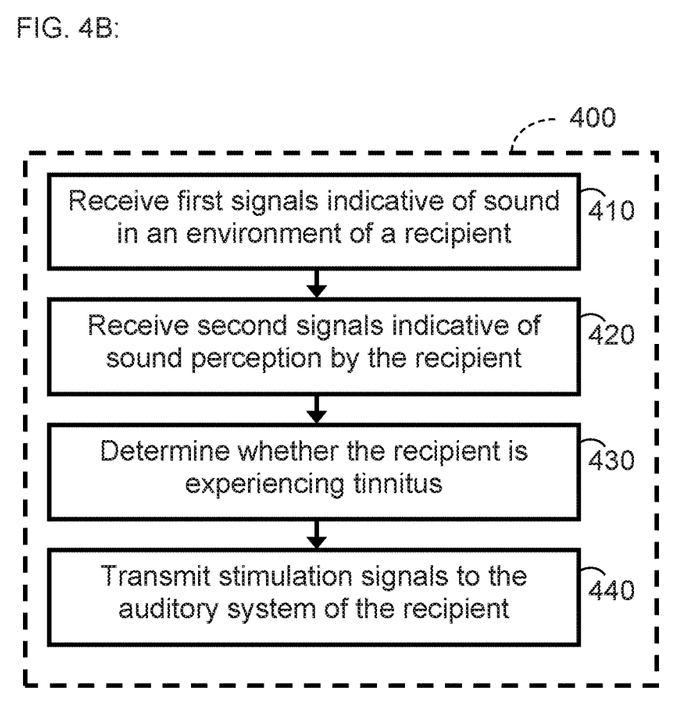

FIGS. 4A and 4B are flow diagrams of two example methods 400 in accordance with certain embodiments described herein. In an operational block 410, the method 400 comprises receiving first signals (e.g., transducer signals 252 received from at least one microphone) indicative of sound in an environment of a recipient. In an operational block 420, the method 400 further comprises receiving second signals (e.g., sensor signals 222; EEG signals) indicative of sound perception by the recipient (e.g., indicative of brain activity associated with sound perception by the recipient). In an operational block 430, the method 400 further comprises determining, in response to the first signals and the second signals, whether the recipient is experiencing tinnitus (e.g., analyzing for the presence of tinnitus). For example, determining whether the recipient is experiencing tinnitus can comprise identifying time periods in which the first signals are indicative of silence in the environment (e.g., the sound in the environment being less than a predetermined magnitude) and in which the second signals are indicative of sound perception by the recipient (e.g., sound perception being greater than a predetermined level). Such coincidence of the lack of sound in the environment with the perception of sound by the recipient can be indicative of the recipient experiencing tinnitus. In an operational block 440, the method 400 of FIG. 4B further comprises transmitting, while the recipient is experiencing tinnitus, stimulation signals to the auditory system of the recipient.

In certain embodiments, the method 400 further comprises configuring the stimulation signals to provide therapy to the recipient for the tinnitus. For example, configuring the stimulation signals can comprise iteratively adjusting at least one portion of an amplitude-frequency spectrum of the stimulation signals in response to the second signals.

In certain embodiments, receiving the first signals, receiving the second signals, determining whether the recipient is experiencing tinnitus, and transmitting the stimulation signals are performed automatically by an auditory prosthesis.

In this way, certain embodiments advantageously provide an active, closed-loop suppression of the tinnitus of the recipient.

Figure 5:
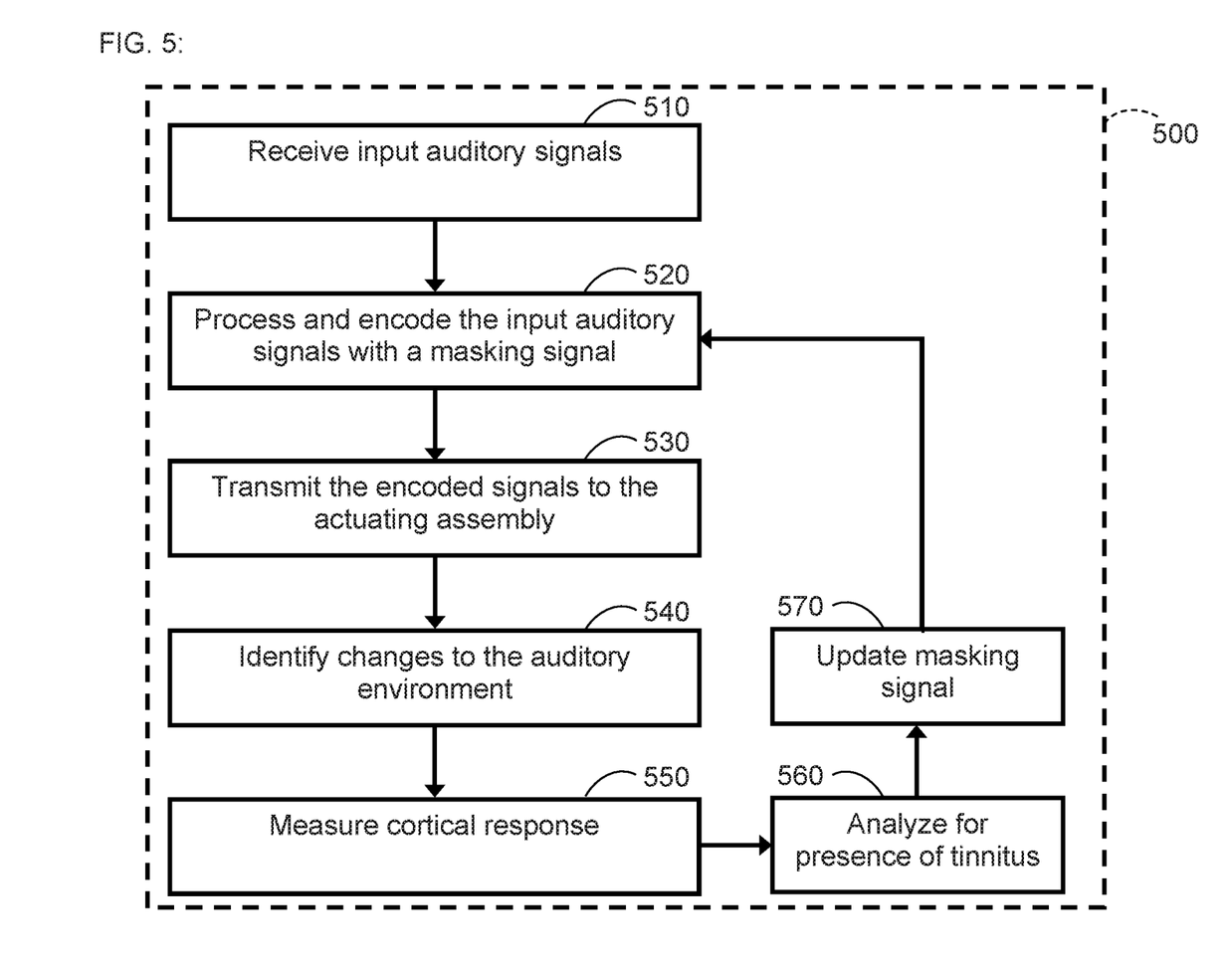
FIG. 5 is a flow diagram of another example method which provides closed-loop tracking of cortical responses to changes in the auditory environment in accordance with certain embodiments described herein.

FIG. 5 is a flow diagram of another example method 500 which provides closed-loop tracking of cortical responses to changes in the auditory environment in accordance with certain embodiments described herein. In an operational block 510, the method 500 comprises receiving input auditory signals (e.g., transducer signals 252 received from at least one microphone) indicative of sound in an environment of a recipient. In an operational block 520, the method 500 further comprises processing and encoding the input auditory signals with a masking signal. For example, the masking signal can correspond to sound (e.g., white noise; music; patterned sound; sound tailored based on characteristics of the recipient's tinnitus) to be added to the sound in the environment of the recipient to mask or cover up the phantom sound (e.g., ringing; hissing) due to tinnitus. The resulting encoded signals (e.g., the data signals 232) have an auditory contribution (e.g., indicative of the sound received by the at least one microphone) mixed with a masking contribution (e.g., indicative of the sound added to mask the phantom sounds). In certain embodiments, receiving the input auditory signals and processing and encoding the input auditory signals with the masking signal are performed by the signal processing circuitry 230.

In an operational block 530, the method 500 further comprises transmitting the resulting encoded signals (e.g., the data signals 232) to the actuating assembly 240 of the auditory prosthesis being worn by the recipient. In an operational block 540, the method 500 further comprises identifying changes to the auditory environment by monitoring the encoded signals for substantial changes (e.g., changes in magnitude or spectral content of the encoded signals greater than or equal to predetermined levels). In certain embodiments, identifying the changes to the auditory environment is performed by the monitoring circuitry 260 receiving the data signals 232.

In an operational block 550, the method 500 further comprises measuring a cortical response of the recipient. In certain embodiments, one or more cortical measurements (e.g., configured to detect one or more MMN responses and/or P100 responses) are triggered upon detecting a substantial change to the auditory environment. In certain embodiments, a programmable delay is introduced upon detecting the substantial change to the auditory environment and before initiating the cortical measurements, and the programmable delay can be variable across different recipients (e.g., to account for the different processing latencies to changes by different recipients). For example, to correlate a measured cortical response with an incoming signal, the measured cortical response can be buffered and aligned post hoc, or the measurement can be delayed to the anticipated time of the event to better (e.g., more easily) correlate the cortical response to the input signal. In certain embodiments, the programmable delay can limit the amount of cortical measurement data that is recorded. In certain embodiments, the cortical measurements are aggregated in a time-weighted average to reduce the effects of noise. Example averaging schemes can include, but are not limited to:

$$\text{epoch}_{mean(n)} = \alpha * \text{epoch}_n + (1-\alpha) * \text{epoch}_{mean(n-1)}, \text{ where } \alpha \in (0,1).$$

In certain embodiments, upon detecting a substantial change to the auditory environment (e.g., as expressed in the data signals 232), the monitoring circuitry 260 can transmit a monitoring signal 262 to the tinnitus analysis circuitry 270, and measuring the cortical response of the recipient can be performed by the cortical measurement assembly 280 under the control of the tinnitus analysis circuitry 270 which can receive the cortical measurements (e.g., sensor signals 222).

In an operational block 560, the method 500 further comprises analyzing the cortical measurements for the presence of tinnitus. In certain embodiments, the magnitude of at least one cortical response (e.g., one or more MMN responses and/or P100 responses) is compared to a corresponding level or threshold. In certain embodiments, the threshold is predetermined (e.g., a previously calibrated level or a long-term reference level). In certain other embodiments, the threshold is adaptively adjusted. For example, the threshold can be adaptively changed in response to the input/output ratio. For another example, the thresholds can also be mediated by a secondary response (e.g., the P100 threshold can be mediated based on the P300 magnitude, or vice versa, as these responses are both attention mediate although to differing degrees). In certain other embodiments, rather than comparing to a corresponding level or threshold, changes in the magnitude of the cortical measurements that are statistical outliers can be used as an indication of tinnitus.

In an operational block 570, the method 500 further comprises updating the masking signal to be mixed with the input auditory signals in the operational block 520. Depending on the comparison of the at least one cortical response to the corresponding predetermined level, one or more characteristics (e.g., amplitude; spectral content) of the masking signal can be updated to improve the degree of masking of the phantom sounds. In certain embodiments, analyzing the cortical measurements is performed by the tinnitus analysis circuitry 270, which generates the detection signals 272 indicative of the presence or absence of tinnitus and transmits the detection signals 272 to the masker circuitry 290. In certain embodiments, updating the masking signal is performed by the masker circuitry 290 in response to the detection signals 272, and the masker circuitry 290 generates the control signals 212 (e.g., indicative of the masking signal to be mixed with the input auditory signals) and transmits the control signals 212 to the signal processing circuitry 230.

Figure 6:
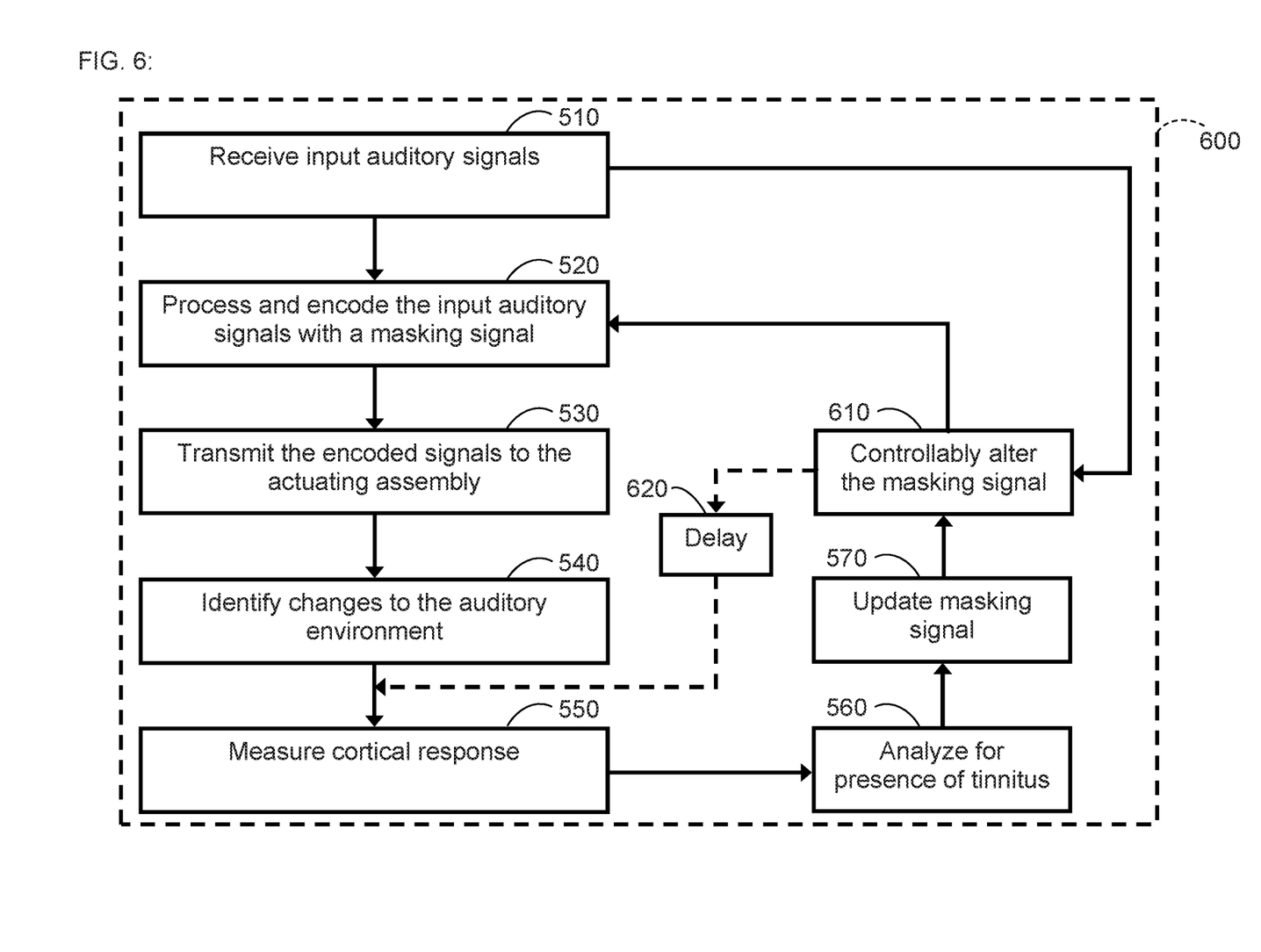
FIG. 6 is a flow diagram of another example method which provides closed-loop tracking of cortical responses to controlled alterations in the masker in accordance with certain embodiments described herein.

FIG. 6 is a flow diagram of another example method 600 which provides closed-loop tracking of cortical responses to controlled alterations in the masker in accordance with certain embodiments described herein. The method 600 comprises the operational blocks 510-570 described herein with regard to the example method 500 of FIG. 5. In an operational block 610, the method 600 further comprises controllably altering the masking signal after updating the masking signal in the operational block 570. In certain embodiments, a predetermined function is used to controllably alter the masking signal (e.g., at pseudo-random times when the recipient is in a quiet auditory environment) and the altered masking signal is mixed with the input auditory signals in the operational block 520. For example, controllably altering the masking signal can comprise introducing a gap (e.g., a relatively short time period during which the masking signal is reduced or zero) in an otherwise constant masking signal. In certain embodiments, this altering of the masking signal can be accompanied by a triggering of one or more measurements of the cortical response in the operational block 550. As schematically illustrated by the delay block 620 of FIG. 6, the triggering of the one or more cortical response measurements can be performed after a programmable delay corresponding to the known timing of when the altered masking signal is to be presented to the recipient (e.g., by the signal processing circuitry 230 and the actuating assembly 240). In certain embodiments, controllably altering the masking signal is performed by the masker circuitry 290.

Figure 7:
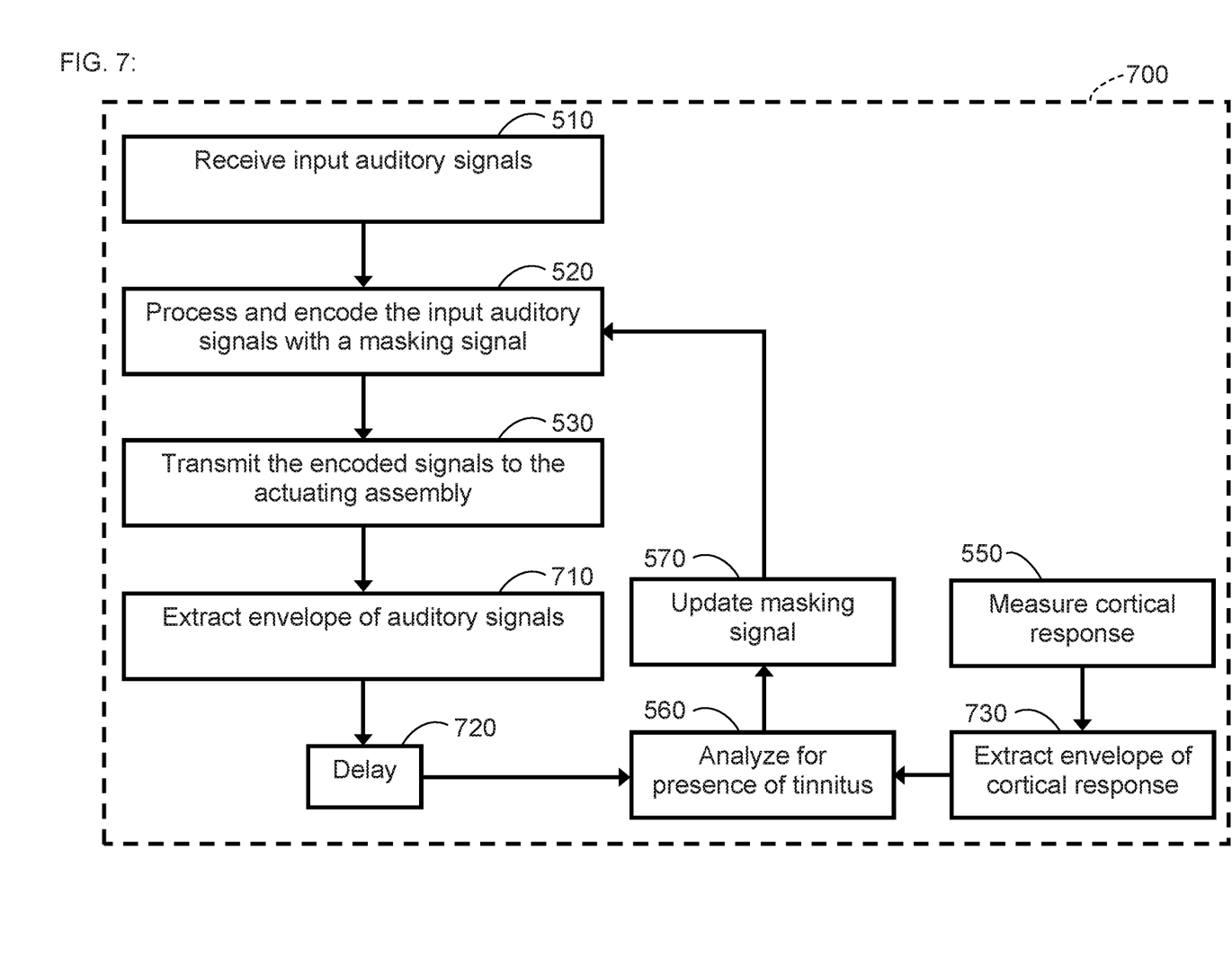
FIG. 7 is a flow diagram of another example method which provides closed-loop tracking of cortical response envelopes to address attentional changes in accordance with certain embodiments described herein.

FIG. 7 is a flow diagram of another example method 700 which provides closed-loop tracking of cortical response envelopes to address attentional changes in accordance with certain embodiments described herein. Higher level cortical response magnitudes (e.g., MMN magnitudes) are attentionally related (e.g., the magnitude of the response is enhanced if the recipient is paying attention to the auditory stimulus). The method 700 of FIG. 7 is configured to provide a level of refinement to the closed loop control of tinnitus treatment by correlating the EEG response in the temporal cortex (e.g., an envelope of the cortical response) with the auditory signals provided to the recipient (e.g., an envelope of the delivered audio) to which the recipient is paying attention. In certain embodiments, the attentional behavior is used as a metric to scale the expected cortical responses (e.g., the expected cortical MMN responses and/or P100 responses) to substantial changes to the delivered auditory output.

The method 700 comprises the operational blocks 510-530 and 550-570 described herein with regard to the example method 500 of FIG. 5. The method 700 comprises extracting an envelope of the auditory signals delivered to the recipient in an operational block 710 (e.g., performed by the monitoring circuitry 260) and providing the extracted envelope for analysis (e.g., providing the extracted envelope to the tinnitus analysis circuitry 270 for analysis) after a programmable delay as schematically illustrated by the delay block 720 of FIG. 7. In an operational block 730, the method 700 further comprises extracting an envelope of the measured cortical response (e.g., measured in the operational block 550 using the cortical measurement assembly 280) and providing the extracted envelope for analysis (e.g., providing the extracted envelope to the tinnitus analysis circuitry 270 for analysis). Analyzing for the presence of tinnitus in the operational block 560 can comprise comparing the extracted envelope of the auditory signals and the extracted envelope of the measured cortical response and identifying correlations of the extracted envelopes. Updating the masking signal in the operational block 570 (e.g., performed by the masker circuitry 290) can comprise using information regarding the correlated extracted envelopes to generate updates of the masking signal which is to be mixed with the input auditory signals in the operational block 520.

Figure 8:
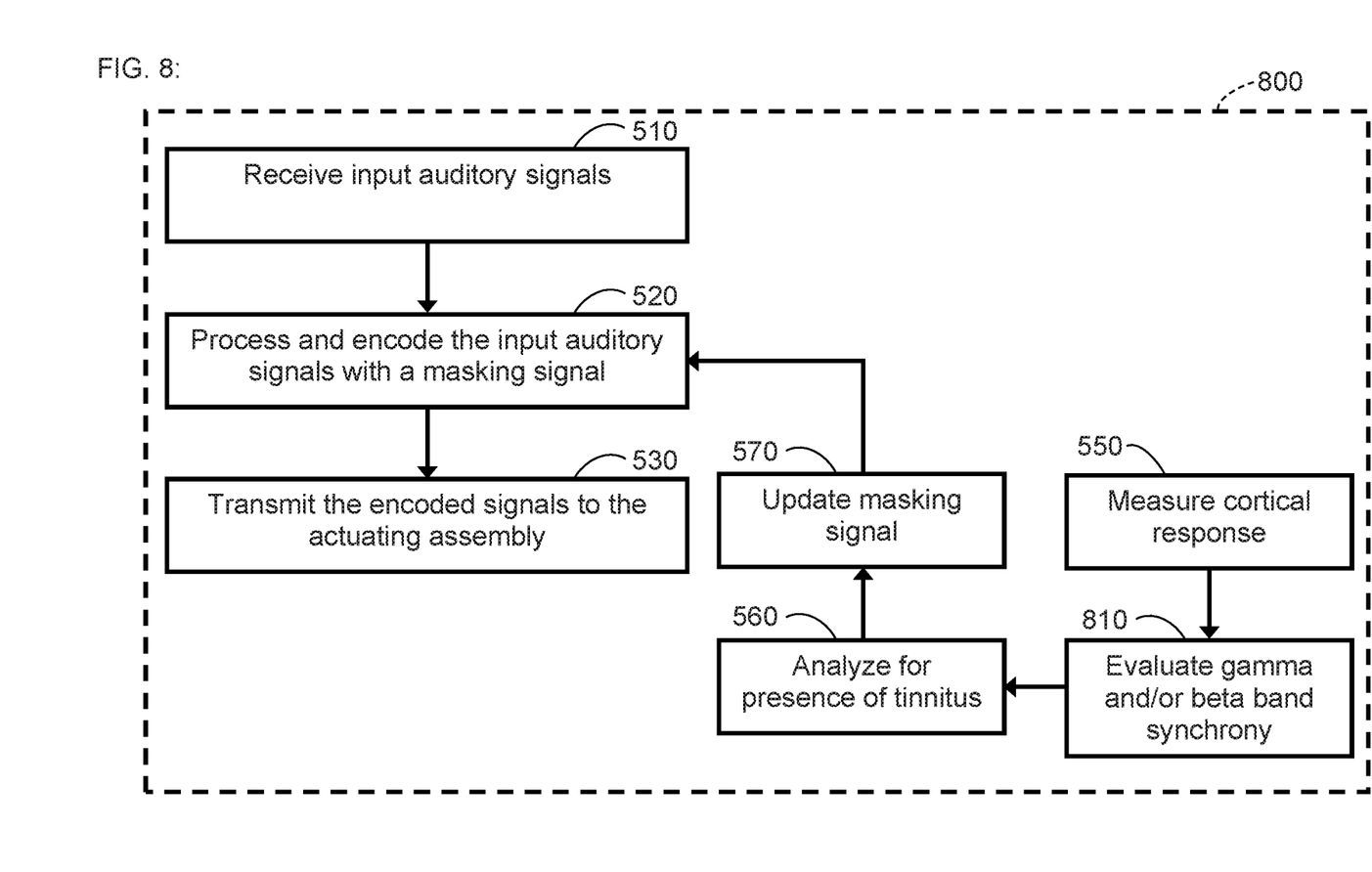
FIG. 8 is a flow diagram of another example method which modifies the tinnitus treatment in response to detected distress (e.g., gamma band synchrony) associated with tinnitus in accordance with certain embodiments described herein.

FIG. 8 is a flow diagram of another example method 800 which modifies the tinnitus treatment in response to detected distress (e.g., gamma band synchrony) associated with tinnitus in accordance with certain embodiments described herein. In some circumstances, the presence of tinnitus is not an issue to be treated if the recipient is not paying attention to it and/or is not aggravated by it, and at certain times, the presence of a masker signal may be detrimental to the recipient and/or the overall treatment. In certain embodiments, the example method 800 comprise monitoring the cortical response for features (e.g., gamma band synchrony and/or beta band synchrony) associated with distress (e.g., tinnitus-associated distress) and providing the masking signals to the recipient (e.g., applying the tinnitus treatment) and/or modifying the masking signals only if the recipient is exhibiting signs of distress which may be associated with the presence of tinnitus.

The method 800 comprises the operational blocks 510-530 and 550-570 described herein with regard to the example method 500 of FIG. 5. In the operational block 810, the method 800 comprises extracting information regarding the gamma band synchrony and/or beta band synchrony of the measured cortical response (e.g., provided in the operational block 550 by the cortical measurement assembly 580). The method 800 further comprises analyzing for the presence of tinnitus (e.g., analyzing the information for indications that the recipient is experiencing distress possibly due to tinnitus) in the operational block 560. For example, the operational blocks 560 and 810 can be performed by the tinnitus analysis circuitry 270. The method 800 further comprises updating the masking signal in the operational block 570 (e.g., performed by the masker circuitry 290) which is to be mixed with the input auditory signals in the operational block 520.

Certain embodiments described herein are configured to detect pulsatile sounds and/or phantom sounds due to pulsatile tinnitus (e.g., corresponding to the recipient's heartbeat) and to provide a corresponding treatment. For example, the biological monitor 220 can further comprise a heart rate monitor configured to detect the recipient's heartbeat and to provide sensor signals 222 that are used by the control circuitry 210 to adjust the temporal characteristics of the masking signals to treat (e.g., mask; counteract) the pulsatile sounds and/or phantom sounds.

In certain embodiments, the biological monitor 220 comprises a functional near infrared spectroscopy (fNIRS) monitor configured to utilize infrared light (e.g., different wavelengths) to detect blood oxygenation. In certain such embodiments, an fNIRS matrix of light sources is positioned on the recipient's skin or are implanted within or below the recipient's skin. For example, the fNIRS matrix can be used in place of EEG electrodes. While the fNIRS monitor has some similarity to pulse oximetry sensors, unlike pulse oximetry sensors, the fNIRS monitor comprises a plurality of light sources each associates with multiple receptors, allowing for localization of the section of the brain where oxygen take-up is occurring. Increased utilization of oxygen is strongly correlated with the level of brain activity, so in certain embodiments, the fNIRS monitor is used to measure some of the same phenomena as are EEG monitors, but with improved spatial resolution and decreased temporal resolution. While the morphology and time constants of the fNIRS signals are different from those of EEG signals, in certain embodiments, fNIRS signals are used to identify the MMN response, as well as for tracking low frequency brain oscillations, as an alternative to EEG measurements or as an additional supplement to EEG measurements.

It is to be appreciated that the embodiments disclosed herein are not mutually exclusive and may be combined with one another in various arrangements.

The invention described and claimed herein is not to be limited in scope by the specific example embodiments herein disclosed, since these embodiments are intended as illustrations, and not limitations, of several aspects of the invention. Any equivalent embodiments are intended to be within the scope of this invention. Indeed, various modifications of the invention in form and detail, in addition to those shown and described herein, will become apparent to those skilled in the art from the foregoing description. Such modifications are also intended to fall within the scope of the claims. The breadth and scope of the invention should not be limited by any of the example embodiments disclosed herein, but should be defined only in accordance with the claims and their equivalents.

What is claimed is:

1. A method comprising:
   receiving first signals from at least one microphone, the first signals indicative of sound in an environment of a recipient and evaluating the first signals to detect one or more aspects of the sound that are indicative of the recipient potentially experiencing tinnitus-associated distress;
   receiving second signals from at least one biological monitor of brain activity of the recipient, the second signals indicative of sound perception by the recipient;
   in response to detecting the one or more aspects, analyze the second signals to determine whether the recipient is experiencing tinnitus-associated distress; and
   while the recipient is experiencing tinnitus-associated distress, transmitting stimulation signals to an auditory system of the recipient, the stimulation signals configured to provide therapy to the recipient for the tinnitus-associated distress.

2. The method of claim 1, wherein the stimulation signals are configured by iteratively adjusting at least one portion of an amplitude-frequency spectrum of the stimulation signals in response to the second signals.

3. The method of claim 1, wherein receiving the first signals, receiving the second signals, determining whether the recipient is experiencing tinnitus-associated distress, and transmitting the stimulation signals are performed automatically by an auditory device.

4. The method of claim 1, wherein the second signals comprise electroencephalogram (EEG) signals.

5. An apparatus comprising:
   an actuating assembly of a device worn by a recipient, the actuating assembly configured to transmit stimulation signals to an auditory system of the recipient;
   signal processing circuitry configured to receive transducer signals from at least one acoustic transducer and to generate data signals in response at least in part to the transducer signals, the transducer signals indicative of sound received from an auditory environment by the at least one acoustic transducer, the signal processing circuitry further configured to transmit the data signals to the actuating assembly; and
   control circuitry configured to:
     receive sensor signals indicative of a cortical response of the recipient, the cortical response associated with phantom sound perception by the recipient;
     monitor the data signals, the transducer signals, or both the data signals and the transducer signals for at least one attribute of the auditory environment indicative of the recipient potentially perceiving phantom sound;
     in response to detecting the at least one attribute, analyze the sensor signals to determine whether the recipient is perceiving phantom sounds; and
     generate control signals in response at least in part to the sensor signals and the data signals, the signal processing circuitry further configured to generate the data signals in response at least in part to the control signals generated by the control circuitry, the stimulation signals transmitted by the actuating assembly in response to the data signals configured to at least partially alleviate phantom-sound-based discomfort of the recipient and/or to at least partially mask the phantom sound perception by the recipient.

6. The apparatus of claim 5, wherein the control circuitry is further configured to automatically generate the control signals in response at least in part to the transducer signals.

7. The apparatus of claim 5, wherein the control circuitry is further configured to automatically generate the control signals in response at least in part to the data signals.

8. The apparatus of claim 5, wherein the cortical response comprises a neural response and the sensor signals comprise EEG signals and/or fNIRS signals.

9. The apparatus of claim 5, wherein the control circuitry and the signal processing circuitry are in a closed-loop configuration.

10. An apparatus comprising:
    at least one actuating assembly of a device worn by or implanted within a recipient, the actuating assembly configured to generate and transmit stimulation signals to an auditory system of the recipient;
    at least one acoustic transducer configured to generate transducer signals indicative of sound in an environment of the recipient;
    signal processing circuitry configured to receive transducer signals indicative of sound received by the at least one acoustic transducer and to generate data signals to be provided to the at least one actuating assembly; and
    control circuitry configured to:
        evaluate the transducer signals to detect one or more aspects of the sound that are indicative of the recipient potentially experiencing tinnitus;
        monitor the data signals and cortical sensor signals indicative of a neural response of the recipient;
        generate and provide control signals to the signal processing circuitry in response to detection of the one or more aspects with the neural response being indicative of distress associated with tinnitus being experienced by the recipient, the control signals indicative of a masking contribution to be included in the data signals received by the at least one actuating assembly, the stimulation signals having a portion corresponding to the masking contribution such that the stimulation signals at least partially mask the tinnitus being experienced by the recipient,
    the signal processing circuitry further configured to respond to the control signals by modifying the masking contribution of the data signals such that the signal processing circuitry, the at least one actuating assembly, and the control circuitry provide active, automated, closed-loop suppression of tinnitus effects.

11. The apparatus of claim 10, wherein the cortical sensor signals comprise electroencephalogram (EEG) signals indicative of the neural response of the recipient.

12. The apparatus of claim 10, wherein the cortical sensor signals comprise functional near infrared spectroscopy (fNIRS) signals indicative of the neural response of the recipient.

13. The apparatus of claim 10, wherein the control circuitry is further configured to receive signals from a heart rate monitor configured to detect the recipient's heartbeat, the control circuitry further configured to adjust temporal characteristics of the masking contribution to mask pulsatile tinnitus being experienced by the recipient.

14. The apparatus of claim 10, wherein the control circuitry comprises:
    monitoring circuitry configured to monitor the transducer signals, the data signals, or both the transducer signals and the data signals and to generate monitoring signals indicative of one or more characteristics of an auditory environment of the recipient and/or changes of the one or more characteristics;
    analysis circuitry configured to receive the monitoring signals and sensor signals indicative of the neural response of the recipient and to generate detection signals indicative of the tinnitus being experienced by the recipient; and
    masker circuitry configured to generate the control signals in response at least in part to the detection signals.

15. A method comprising:
    receiving first signals from at least one acoustic transducer, the first signals indicative of sound in an environment of a recipient and generating filtered data signals in response to the first signals;
    evaluating the filtered data signals to detect one or more predetermined characteristics of the sound and/or changes of the one or more predetermined characteristics of the sound, the one or more predetermined characteristics and/or the changes of the one or more predetermined characteristics indicative of the recipient potentially experiencing tinnitus;
    receiving second signals from at least one cortical response sensor, the second signals indicative of sound perception by the recipient;
    in response to detecting the one or more predetermined characteristics and/or the changes of the one or more predetermined characteristics, analyze the second signals to determine whether the recipient is experiencing tinnitus; and
    while the recipient is experiencing tinnitus, in response to the filtered data signals, generating and transmitting stimulation signals to an auditory system of the recipient, the stimulation signals configured to provide therapy to the recipient for the tinnitus.

16. The method of claim 15, wherein the one or more predetermined characteristics are selected from the group consisting of: amplitude, frequency, spectral content, and noise level.

17. The apparatus of claim 5, wherein the control circuitry is further configured to receive the sensor signals from a biological monitor and to transmit a triggering signal to the biological monitor in response to detecting the at least one attribute.

18. The apparatus of claim 10, wherein the signal processing circuitry and the control circuitry provide closed-loop tracking of at least one of: cortical responses to changes in the sound, cortical response to controlled alterations in the masking contribution, and cortical response envelopes to address attentional changes of the recipient.

19. The method of claim 1, wherein the stimulation signals are moderated by a level of the tinnitus-associated distress experienced by the recipient.

20. The apparatus of claim 1, wherein the second signals comprise one or more measurement signals indicative of at least one cortical response of the recipient.

21. The apparatus of claim 20, wherein the one or more measurement signals comprise EEG measurements and/or fNIRS measurements.

22. The apparatus of claim 20, wherein the at least one cortical response comprises one or more mismatch negativity (MMN) responses and/or P100 responses.

23. The apparatus of claim 20, wherein the at least one cortical response comprises activation in a gamma band and/or a beta band of a contralateral auditory cortex of the recipient.

* * * * *